United States Patent
Monge Vega et al.

(10) Patent No.: US 6,262,056 B1
(45) Date of Patent: Jul. 17, 2001

(54) BENZOTHIOPHENE DERIVATIVES AND CORRESPONDING USE AND COMPOSITION

(75) Inventors: Antonio Monge Vega, Navarra; Joaquín Del Rio Zambrana, Madrid; Berta Lasheras Aldaz; Juan Antonio Palop Cubillo, both of Navarra; Anna Bosch Rovira, Barcelona; Juan Carlos Del Castillo Nieto, Barcelona; Juan Roca Acin, Barcelona, all of (ES)

(73) Assignee: Vita-Invest, SA, Barcelona (ES)

( * ) Notice: Subject to any disclaimer, the term of this patent is extended or adjusted under 35 U.S.C. 154(b) by 0 days.

(21) Appl. No.: 09/480,120

(22) Filed: Jan. 10, 2000

Related U.S. Application Data

(63) Continuation-in-part of application No. PCT/ES98/00191, filed on Jul. 1, 1998.

(30) Foreign Application Priority Data

Jul. 8, 1997 (ES) .................................................. 9701517

(51) Int. Cl.⁷ ........................ A61K 31/496; C07D 407/06
(52) U.S. Cl. ....................................... 514/252.13; 544/376
(58) Field of Search ........................... 544/376; 514/253, 514/252.13

(56) References Cited

U.S. PATENT DOCUMENTS

| | | | |
|---|---|---|---|
| 2,979,507 | 4/1961 | Janssen | 544/379 |
| 3,002,976 | 10/1961 | Janssen | 544/379 |
| 4,515,793 | 5/1985 | Werbel et al. | 514/252 |
| 5,632,898 | * 5/1997 | Jung et al. | 210/656 |

FOREIGN PATENT DOCUMENTS

| | | |
|---|---|---|
| 0 574 313 A1 | 12/1993 | (EP) . |
| 0 596 120 A1 | 5/1994 | (EP) . |
| 1096341 | 12/1967 | (GB) . |

* cited by examiner

Primary Examiner—Emily Bernhardt
(74) Attorney, Agent, or Firm—Sughrue, Mion, Zinn, Macpeak & Seas, PLLC

(57) ABSTRACT

Benzothiophene derivative compounds and corresponding use and composition; the compounds respond to formula (I):

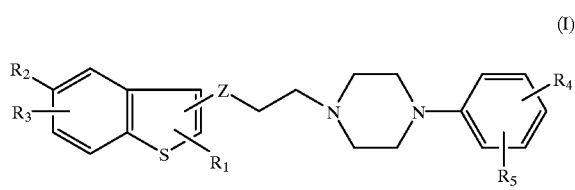

where Z is: —CO—, —CH(OR$_6$)—, —C(NOR$_7$)—; R$_1$ is: H, C$_1$–C$_6$ alkyl, halogen, or —OR$_8$; R$_2$ and R$_3$ are: H, alkyl, halogen, —OR$_8$, nitro, cyano, NR$_9$R$_{10}$; —COR$_8$; CO$_2$R$_8$; —SO$_2$NR$_9$R$_{10}$; —SO$_2$R$_8$; —SR$_8$; —CONR$_9$R$_{10}$; R$_4$ and R$_5$ are: H, alkyl, halogen, haloalkyl, —OR$_8$, nitro, NR$_9$R$_{10}$; —COR$_8$; CO$_2$R$_8$; —SO$_2$NR$_9$R$_{10}$; —SO$_2$R$_8$; SR$_8$, cyano; —CONR$_9$R$_{10}$ or R$_4$ and R$_5$ form a benzene ring; R$_6$ is: H, alkyl, CO$_2$R$_8$, —C(O)NR$_9$R$_{10}$, naphthyl or phenyl; R$_7$ is: H or alkyl; R$_8$ is H, C$_1$–C$_6$ alkyl or phenyl; R$_9$ and R$_{10}$ are: H, alkyl or phenyl or R$_9$ and R$_{10}$ form a 5- or 6-membered ring. These compounds are effective for the treatment of anxiety or depression.

7 Claims, No Drawings

BENZOTHIOPHENE DERIVATIVES AND CORRESPONDING USE AND COMPOSITION

This application is a continuation-in-part application of PCT Application PCT/ES98/00191, filed Jul. 1, 1998

FIELD OF THE INVENTION

The present invention relates to the synthesis of new benzothiophene derivatives, the salts, optical isomers and polymorphs thereof, having the general formula (1)

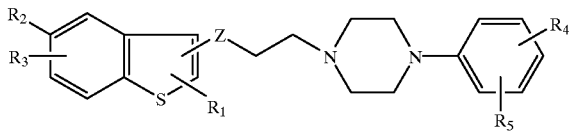

as also to the corresponding pharmaceutical compositions and the use thereof in the preparation of these pharmaceutical compositions for the treatment of neurological disorders and, in particular, for the treatment of anxiety and/or depression, as being antidepressants having a dual activity: inhibition of serotonin reuptake and having affinity for the $5\text{-}HT_{1A}$ receptor.

BACKGROUND OF THE INVENTION

Drugs for the treatment of depression have been available for over 30 years. Both the first monoamino oxidase inhibitor (MAO inhibitor), iproniazide, and the first tricyclic antidepressant (T.ACA), imipramine, were placed on the market at the end of the 50's. The second generation antidepressants represent a considerable improvement on the traditional tricyclic antidepressants, or on the irreversible unspecific MAO inhibitors. In spite of this, they still offer side effects, and what is more important, the latency time until the therapeutic effect appears is still too long for the treatment to be deemed optimal.

The latest class of antidepressants placed on the market was the one comprising the selective serotonin reuptake inhibitors, outstanding among which are fluoxetine (Lilly ES433720), paroxetine (Ferrosan, ES422734) and sertraline (Pfizer, ES496443). The products of this class have a high degree of structural diversity in comparison with other types of serotonin reuptake inhibitors, such as may be the tricyclic antidepressants. In spite of their structural variety, these compounds are highly selective for the serotonin receptor. In fact, their binding to α and β adrenergic, dopaminergic., histamine and muscarine receptors is insignificant. It is postulated that this could be due to a great structural similarity to the pharmacophore, which is responsible for their specificity, and relative affinity to the corresponding serotonin receptor.

Among the most frequent adverse effects of the serotonin reuptake inhibitors are those related with gastrointestinal disorders. The majority of them also cause inhibition of the hepatic metabolism of other drugs with the corresponding pharmaco-dynamic interactions and have a retarded onset of their antidepressive action.

With this background in mind, there arises the need to continue investigating so as to create a third generation of antidepressants. The four points that an antidepressant must fulfil to be considered as a member of the third generation are:

1. Faster action
2. Broader efficacy
3. Less side effects
4. Safer in case of overdose The first of these four points is the one offering the greatest challenge in antidepressant research since the harm that it represents for a depression patient that the drug does not start to show its effects until the elapse of several weeks after the start of the treatment is obvious.

The reason why the ailment takes time to remit, after treatment with monoamine reuptake inhibitors, appears to be due to a process of desensitisation of the presynaptic $5\text{-}HT_{1A}$ receptors, which means that the serotoninergic tone is reduced until this desensitisation has occurred.

It may be gathered from all the above that an antidepressive treatment which, further to inhibiting the serotonin reuptake, were to involve a blocking or a rapid desensitisation of the $5\text{-}HT_{1A}$ somatodentritic autoreceptors would increase the antidepressive effectiveness, on allowing the serotonin concentration in the serotoninergic terminations to rise quickly. In this sense, there has been proposed the simultaneous administration of serotonin reuptake inhibitors with selective $5\text{-}HT_{1A}$ receptor antagonists, such as pindolol (Artigas F. et al., Arch. Gen. Psychiatry, 51, 248–251 (1994); Blier P. et al., J. Clin. Pharmacol. 15, 217–222 (1995)) to facilitate the quickest possible onset of the antidepressive effect. This theory has led the researchers suggest that the addition of products blocking the $5\text{-}HT_{1A}$ type autoreceptors may prevent the onset of this negative feedback system and potentiate the effect of the serotonin reuptake inhibitors.

One Lilly patent (EP 0 687 472) claims the potentiation of the effect of the serotonin reuptake inhibitors by increasing the availability of certain brain neurotransmitters (serotonin among them) by combining the serotonin reuptake inhibitors with selective $5\text{-}HT_{1A}$ receptor antagonists.

Bearing the above background in mind, it is therefore an object of this invention to synthesise compounds having this dual activity, i.e., serotonin reuptake inhibitors with affinity for the $5\text{-}HT_{1A}$ receptor.

The invention relates in particular to the synthesis and pharmacological activity of new benzothiophene derivatives of the general formula (1).

Products to some extent similar to those disclosed here have been claimed in the literature. Thus, for example, U.S. Pat. No. 2,979,507 claims products having the general formula:

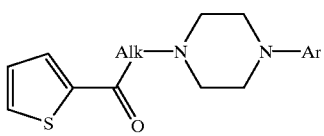

To be precise, there are disclosed the products:

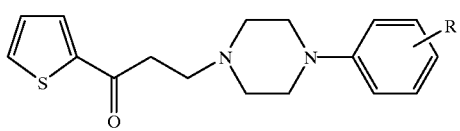

where R may be H or $2\text{-}OCH_3$ among others.

The document EP 0 596 120 claims products of the general formula:

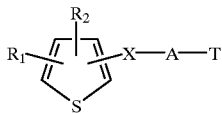

where X is generally: —S, or S(O)— but may be, among others: —C(O)—; —CH(OR)—; —C(N—OR)—; —CH(NH$_2$)—; A may be an alkylene group and T is generally a 1,2-benzoisoxazole or 1,2-benzothiazole ring, but may be any other aromatic ring. Nevertheless, the above document does not contemplate the possibility of R$_1$ and R$_2$ jointly forming a ring, whereby the products claimed do not include benzothiophenes.

The document GB 1096341 discloses products of the general formula

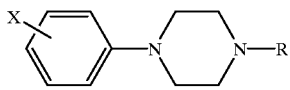

where R may be: —CH$_2$—CH$_2$—C(O)—Ar and Ar may be, among others, a thiophene ring, although not a benzothiophene ring.

To be precise, the above patent describes the products:

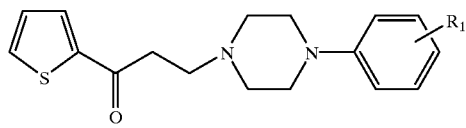

where R$_1$ is 2-F or 4-F or 4-Cl.

U.S. Pat. No. 3,002,976 claims compounds of the general formula:

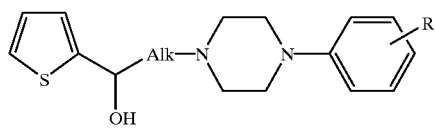

where R is H, methyl or halogen.

The documents WO 9616052 and WO 9615792, describe products of general formula:

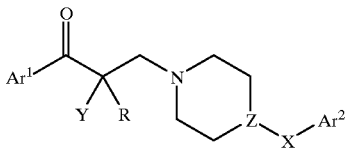

where Z is N or CH, and Ar$^1$ may be a benzothiophene ring. In these compounds the aromatic ring (Ar$^2$) is not directly attached to the piperazine ring, but through a spacer X (CH$_2$, CO, etc.), unlike the compounds of the present invention.

The document DE 2360545 describes piperazines including the compound:

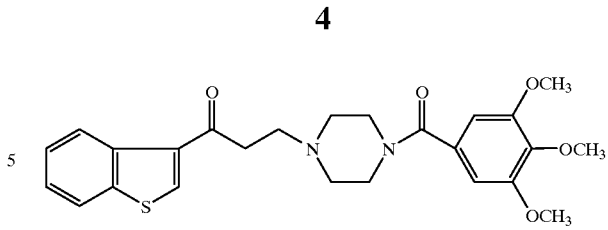

benzothiophene which, like the above named compounds, does not have the aromatic ring directly attached to the piperazine.

DESCRIPTION OF THE INVENTION

As stated above, the object of the present invention are new benzothiophene derivatives of the general formula (1), and the corresponding compositions and the use thereof for obtaining compositions having a pharmacological activity.

(I)

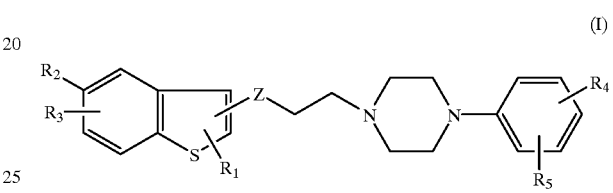

where

Z is: —CO—, —CH(OR$_6$)—, —C(NOR$_7$)—;

R$_1$ is: H, low molecular weight alkyl, halogen, or —OR$_8$;

R$_2$ and R$_3$ are independent and stand for: H, C$_1$–C$_6$ alkyl, halogen, —OR$_8$, nitro, cyano, NR$_9$R$_{10}$, —COR$_8$, —CO$_2$R$_8$, —SO$_2$NR$_9$R$_{10}$, —SO$_2$R$_8$, —SR$_8$, —CONR$_9$R$_{10}$;

R$_4$ and R$_5$ are the same or different and each stands for: H, C$_1$–C$_6$ alkyl, halogen, haloalkyl, —OR$_8$, nitro, NR$_9$R$_{10}$; —COR$_8$; CO$_2$—R$_8$; —SO$_2$NR$_9$R$_{10}$; —SO$_2$R$_8$; SR$_8$, cyano; —CONR$_9$R$_{10}$ or R$_4$ and R$_5$ may form together a benzene ring fused to the phenyl ring;

R$_6$ is: H, C$_1$–C$_6$ alkyl, CO$_2$R$_8$, —C(O)NR$_9$R$_{10}$, naphthyl or phenyl optionally substituted by one or more substituents selected from among the following: H, haloalkyl, C$_1$–C$_6$ alkyl, halogen, C$_1$–C$_6$ alkoxy, methylenedioxy, nitro, cyano;

R$_7$ is: H or C$_1$–C$_6$ alkyl;

R$_8$ is H, low molecular weight alkyl or phenyl;

R$_9$ and R$_{10}$ are independent and stand for: H, low molecular weight alkyl or phenyl or R$_9$ and R$_{10}$ together with the N to which they are attached form a 5- or 6-membered ring in which there may optionally be an N, O or S.

The invention also comprises the physiologically acceptable salts, solvates and salts of the solvates of the formula (1) compounds and which include the acid addition salts formed with inorganic and organic acids, for example hydrochlorides, hydrobromides, sulphates, nitrates, phosphates, formates, mesylates, citrates, benzoates, fumarates, maleates, lactates and succinates, among others. When a salt of a formula (I) compound is formed with a dicarboxylic acid, such as succinic acid, the salt may contain between one and two moles of the formula (I) compound per mole of acid.

The preferred salts are the hydrochlorides. The preferred solvates are the hydrates.

The formula (1) compounds also additionally comprise the geometric isomers CIS/TRANS (Z and E) when the Z group stands for: —C(NOR$_7$)—and the optical isomers (R and S) when Z stands for: —CH(OR$_6$)—, as well as the enantiomeric mixtures thereof.

The preferred compounds according to the invention are those of formula (1) where:

Z is: —C(O)—, —CH(OH)—, —CH(OR$_6$)—or —C(NOR$_7$)—attached to the 2- or 3-position of the benzothiophene ring;

R$_1$ is: H or lower alkyl;

R$_2$ and R$_3$ are independent and stand for: H, low molecular weight alkyl, halogen, —OR$_8$, nitro, NR$_9$R$_{10}$;

R$_4$ is H or halogen;

R$_5$ is H, hydroxy or lower alkoxy;

R$_6$ is H or naphthyl;

R$_7$ is H;

R$_8$, R$_9$, R$_{10}$ are independent and stand for: H or alkyl.

The compounds of the present invention are useful for the treatment of disorders related with the serotonin reuptake and other disorders related with the post- or presynaptic transmission of serotonin and in particular for the treatment of depression.

The treatments may be preventive or curative and are carried out by administration by any conventional way of a formula (1) compound or of a physiologically acceptable salt or solvate thereof.

More particularly, the present invention relates to the benzothiophene derivatives having the following chemical names:

1-(benzo[b]thiophen-3-yl)-3-[4-(2-methoxyphenyl)piperazin-1-yl]propan-1-ol 1-(benzo[b]thiophen-3-yl)-3-[4-(2-methoxyphenyl)piperazin-1-yl]propan-1-one 1-(benzo[b]thiophen-3-yl)-3-[4-(2-methoxyphenyl)piperazin-1-yl]propan-1-one oxime 1-(benzo[b]thiophen-3-yl)-3-[4-(2-hydroxyphenyl)piperazin-1-yl]propan-1-ol 1-(3,5-dimethylbenzo[b]thiophen-2-yl)-3-[4-(2-methoxyphenyl)piperazin-1-yl]propan-1-ol 1-(3,5-dimethylbenzo[b]thiophen-2-yl)-3-[4-(2-methoxyphenyl)piperazin-1-yl]propan-1-one 1-(3-methylbenzo[b]thiophen-2-yl)-3-[4-(2-hydroxyphenyl)piperazin-1-yl]propan-1-ol 1-(5-fluorobenzo[b]thiophen-3-yl)-3-[4-(2-methoxyphenyl)piperazin-1-yl]propan-1-one 1-(5-clorobenzo[b]thiophen-3-yl )-3-[4-(2-methoxyphenyl)piperazin-1-yl]propan-1-one 1-(5-clorobenzo[b]thiophen -3-yl)-3-[4-(2-methoxyphenyl)piperazin-1-yl]propan-1-ol 1-(5-fluorobenzo[b]thiophen-3-yl)-3-[4-(2-methoxyphenyl)piperazin-1-yl]propan-1-ol In accordance therewith, the invention also provides an acceptable pharmaceutical composition for use in medicine, comprising: (a) a pharmaceutically effective amount of a formula (1) compound and/or a salt or solvate thereof, and (b) a pharmaceutically acceptable carrier for oral, sublingual, parenteral, retard or intranasal administration or in a form appropriate for administration by inhalation or insufflation.

The invention also relates to the use of a benzothiophene derivative of formula (1) for the preparation of a drug having therapeutical application as an antidepressant.

The pharmaceutical compositions for oral administration may be solid, as for example tablets or capsules prepared by conventional means with pharmaceutically acceptable carriers, or liquids such as for example aqueous or oil solutions, syrups, elixirs, emulsions or suspensions prepared by conventional means with pharmaceutically acceptable additives.

The formula (1) compounds and the physiologically acceptable salts or solvates thereof may be prepared by adaptation of the general methods related below.

DESCRIPTION OF THE SYNTHESIS PROCEDURES

Preparation of the Ketones of Formula (1a)

The ketone derivatives of formula (1a) (Z is C=O)

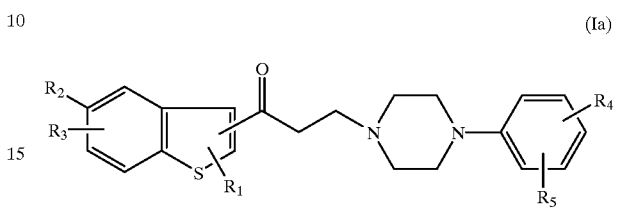

(Ia)

are prepared by:

Method A

A Mannich reaction of the corresponding acylbenzo(b)thiophene with the appropriate piperazine, according to the following reaction:

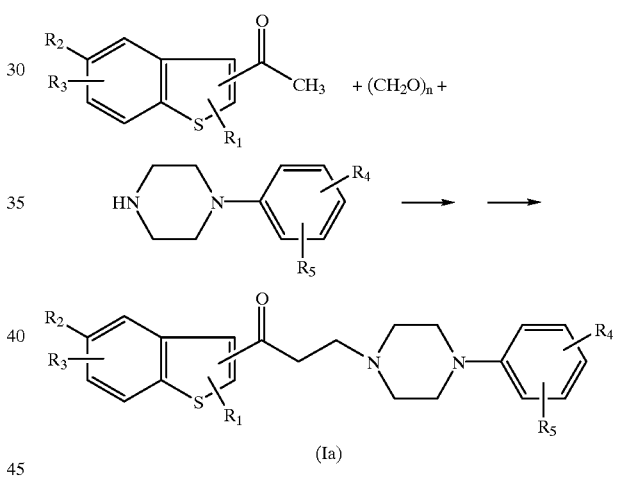

(Ia)

where R$_1$, R$_2$, R$_3$, R$_4$ and R$_5$ have the meanings given above.

Method B

An alternative process for the preparation of the formula (1a) ketones consists of reacting the corresponding 1-aryl-3-halo-1-propanone with the appropriate piperazine, according to the following reaction:

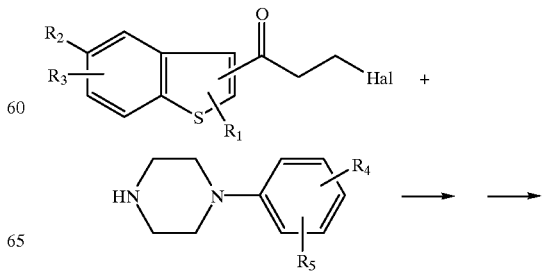

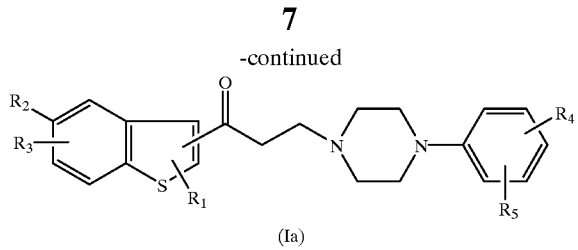

(Ia)

where Hal: halogen.

Method C

A third process for the preparation of the formula (1a) ketones consists of converting, by methods described in the literature, a substituent in a formula (1a) compound into a different substituent, thereby obtaining another different compound responding structurally to the same type of formula (1a). One example of such conversions consists of reducing an aromatic $NO_2$ group by methods described in the literature, to an amino group.

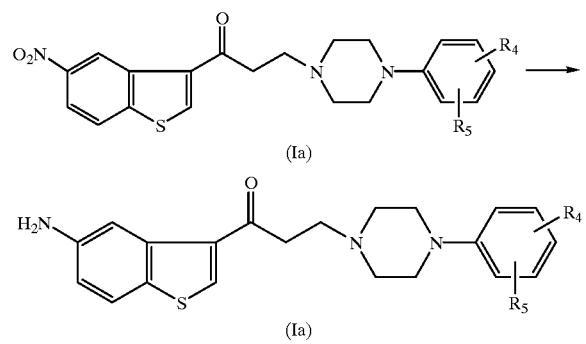

Preparation of the Formula (1b) Alcohols

The alcohol derivatives of formula (1b) (Z is CHOH) are prepared by reducing the ketones (1a) by the regular processes described in the literature, in accordance with the following reaction:

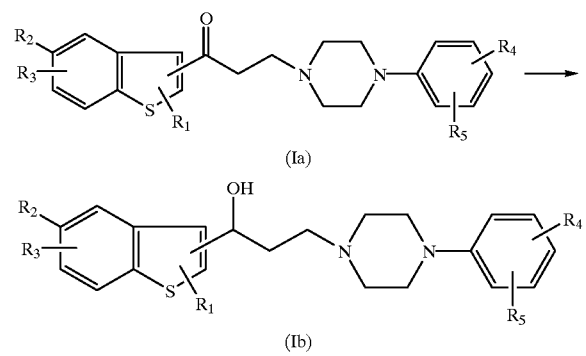

A preferred reduction process consists of using sodium hydroboride as reducing agent in an ethyl or methyl alcoholic medium and at a temperature ranging from −20° C. to the reflux temperature of the corresponding alcohol. The reduction is preferably conducted at 0° C.

Preparation of the Oximes (1c)

The oximes (1c) (Z is C=N—OH) are prepared from the ketones (1a) by the conventional methods described in the literature, a preferred process being the treatment of the ketones (1a) with hydroxylamine hydrochloride in EtOH under reflux.

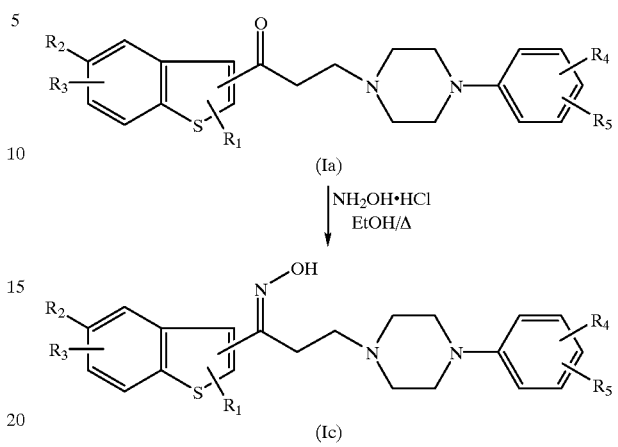

where $R_1$ to $R_5$ have the meanings given above.

The following examples are described with an explanatory, non-limiting purpose.

EXPERIMENTAL

PROCESSES OF SYNTHESIS OF FORMULA (1a) PRODUCTS

Process A

EXAMPLE 1

1-(5-methylbenzo[b]thiochen-3-yl)-3-[4-(2-methoxyphenyl)piperazin-1-yl]propan-1-one dihydrochloride (VN 8312)

1. 3-acetyl-5-methylbenzo(b)thiophene 1 g of 5-methylbenzo(b)thiophene ($6.75 \times 10^{-3}$ moles) was stirred at 55° C. with 0.8 ml of $Ac_2O$ ($8.10 \times 10^{-3}$ moles). 0.83 ml of $BF_3 \cdot Et_2O$ were added and stirring was continued for 8 hours.[11] The solvent was removed in the rotary evaporator and the residue was extracted with AcOEt and $H_2O$. It was decanted and washed with $NaHCO_3$ and $H_2O$. It was dried with $Na_2SO_4$, the solvent was removed and the product was purified in successive columns of AcOEt/hexane (1:1) and toluene respectively. A product was obtained which was a mixture of the substitution isomers in positions 2- and 3- of the benzo(b)thiophene ring in a proportion of approximately 20/80 (determined by the ratios of the areas of the NMR signals), which was passed to the following reaction. Yield: 50%.

The spectroscopic characteristics of the mixture are:

IR($cm^{-1}$): 1668 (mf, C=O)

$^1$H-NMR ($CDCl_3$ 200 MHz) δ(ppm): 2.47 (s, 3H, Ar—$CH_3$ (isomer 2)); 2.50 (s, 3H, Ar—$CH_3$(isomer 3)); 2.63 (s, 3H, CO—$CH_3$ (isomer 2+isomer 3)); 7.22–7.27 (m, 1H, $H_6$) (isomer 2+isomer 3)); 7.66 (s, 1H, $H_3$ (isomer 2)); 7.70–7.76 (m, 1H, $H_7$ (isomer 2+isomer 3)); 7.85 (s, 1H, $H_4$ (isomer 2)); 8.24 (s, 1H, $H_2$(isomer 3)); 8.58 (s,1H, $H_4$ (isomer 3)).

EM-DIP (70 eV) m/z (% Abundance): 190($M^+$)

2. 1-(5-methylbenzo[b]thiophen-3-yl)-3-[4-(2-methoxyphenyl)piperazin-1-yl]propan-1-one dihydrochloride 650 mg of 3-acetyl-5-methylbenzo[b]thiophene ($3.42 \times 10^{-3}$ moles) and 860 mg of 2-methoxyphenylpiperazine hydrochloride ($3.76 \times 10^{-3}$ moles) were dissolved in 15 ml of EtOH and HCl to pH=2–3. When the mixture was under reflux, 310 mg of paraformaldehyde ($10 \times 10^{-3}$ moles) were added. After 24 hours stirring under reflux the reaction mixture was poured over ice and was extracted with AcOEt. It was washed with $H_2O$ and dried with $Na_2SO_4$, the solvent being removed to dryness. It was purified in silica column using AcOEt/hexane (1:1) as mobile phase. The oil obtained was dissolved in ethyl ether (20 ml) and EtOH (4 ml) and precipitates as hydrochloride on adding HCl(c). Yield: 10%.
M.p.=189–190° C.
IR(cm$^{-1}$): 1666 (mf, C=O); 1240 (mf, Ar—O).
$^1$H-NMR (DMSO-d$_6$200 MHz) δ(ppm): 2.46 (s, 3H, Ar—CH$_3$); 3.04–3.76 (m, 12H, —CH$_2$—);3.80 (s, 3H, —O—CH$_3$); 6.88–7.07 (m, 4H, benzene); 7.31 (dd, 1H, H$_6$); 7.98 (d, 1H, H$_7$); 8.44 (s, 1H, H$_2$); 9.08 (s, 1H, H$_4$).
EM-DIP (70 eV) m/z (% Abundance): 394 (M$^+$, 81); 205 (55); 175 (100).

EXAMPLE 2

1-(benzo[b]thiophen-3-yl)-3-[4-(4-fluor-2-methoxyphenyl)piperazin-1-yl]propan-1-one hydrochloride (VN-221F)

1. 2-methoxy-4-fluoroaniline hydrochloride 3.70 g of 3-methoxy-4-nitrofluorobenzene ($21.6 \times 10^{-3}$ moles) were dissolved in 40 ml of MeOH. 0.6 g of Ni-Raney and 4 ml of hydrazine hydrate were added dropwise allowing the mixture to react at 50–55° C. for 2 hours. It was filtered over celite and the solvent was removed. The residue was dissolved in 200 ml of ethyl ether and 2–3 ml of HCl(c) in 40 ml of EtOH were added, thereby obtaining the product, which was collected by filtration. Yield: 65%.
M.p.: 167–168° C.
IR(cm$^{-1}$): 3380 (m, NH$_2$);1245 (mf, Ar—O—).
$^1$H-NMR (CDCl$_3$200 MHz) δ(ppm): 3.83 (s, 3H, OCH$_3$); 6.98–7.24 (m, 3H, benzene); approx. 7.00 (s.a.; 2H, NH$_2$)
EM-DIP (70 eV) m/z (% Abundance): 141 (M$^+$, 6.8)

2. 1-(4-fluoro-2-methoxyphenyl)piperazine 9 ml of chlorobenzene and $H_2O$ were distilled from a solution of 1.14 g of p-TosOH ($6.03 \times 10^{-3}$ moles) in 200 ml of chlorobenzene. The solution was cooled to 20° C. and then 1.19 g of 4-fluor-2-methoxyaniline hydrochloride ($6.7 \times 10^{-3}$ moles) and 1.31 g of bis (2-chloroethyl)amine hydrochloride ($7.36 \times 10^{-3}$ moles) were added. The reaction was held under reflux for 72 hours after which the solvent was removed and the residue was extracted with 5 ml of NaOH 2N and 30 ml of toluene. The organic phase was washed with $H_2O$, was dried with $Na_2SO_4$ and the toluene was removed. The product was purified by silica column using dichloromethane/MeOH (9:1) as mobile phase. An oil was obtained. Yield: 25%.
IR(cm$^{-1}$): 3380 (m, NH$_2$); 1245 (mf, Ar—O—).
$^1$H-NMR (CDCl$_3$200 MHz) δ(ppm): 3.13 (s, 8H, CH$_2$); 4.00 (s, 1H, NH); 3.84 (s, 3H, OCH$_3$), 6.63–6.81 (m, 3H, benzene).
EM-DIP (70 eV) m/z (% Abundance): 210 (M$^+$, 44); 168 (100).

3. 1-(benzo[b]thiophen-3-yl)-3-[4-(4-fluoro-2-methoxyphenyl)piperazin-1-yl]propan-1-one hydrochloride A mixture of 220 mg of 3-acetylbenzo[b]thiophene ($1.25 \times 10^{-3}$ moles) and 263 mg of 1-(4-fluor-2-methoxyphenyl) piperazine ($1.25 \times 10^{-3}$ moles) in 5 ml of EtOH with sufficient HCl(c) for the pH to be equal to 2–3 was heated to reflux. Thereafter 110 mg of paraformaldehyde were added and refluxing was maintained for 8 hours. After this time, the reaction mass was allowed to cool and was poured over ice and $H_2O$. In this way, the hydrochloride of the product precipitated out and was collected by filtration. The filter liquors were basified with NaOH 2N and extracted with AcOEt. The organic phase was washed with $H_2O$ and with a saturated NaCl solution, was dried with $Na_2SO_4$ and the solvent was removed. A further fraction of the product was obtained in a silica column with AcOEt/hexane (1:1) as mobile phase. Yield: 30%.
M.p.: 199–201° C.
IR(cm$^{-1}$): 1671 (f, C=O);
$^1$H-NMR (CDCl$_3$200 MHz) δ(ppm): 2.73 (t, 4H, (CH$_2$)$_2$—N); 2.95 (t, 2H, CO—CH$_2$—CH$_2$); 3.09 (t, 4H, (CH$_2$)$_2$—Ar); 3.25 (t, 2H, CO—CH$_2$)3.83 (s, 3H, O—CH$_3$); 6.60–6.75 (m,3H, benzene); 7.37–7.52 (m, 2H, H$_5$, H$_6$); 7.85 (d, 1H, H$_7$); 8.32 (s, 1H, H$_2$); 8.76 (d,1H, H$_4$).
EM-DIP (70 eV) m/z (% Abundance): 398 (M$^+$; 40); 223 (69); 161 (100)

Using the process described in Examples 1 and 2, the following compounds were prepared:

EXAMPLE 3

1-(benzo[b]thiophen-3-yl)-3-[4-(-2 methoxyphenyl) piperazin-1-yl]propan-1-one hydrochloride. (VN-2212)

M.p.: 214–215° C.
IR(cm$^{-1}$): 1670 (f, C=O); 1243 (mf, Ar—O)
$^1$H-NMR (CDCl$_3$200 MHz) δ(ppm): 2.04–2.16 (m, 2H, CO—CH$_2$); 2.65–2.83 (m, 6H, (CH$_2$)$_3$—N); 2.97 (t, 4H, (CH$_2$)$_2$—N—Ar); 5.36 (dd, 1H, CHOH); 6.70 (s.a.1H, OH); 6.95–7.00 (s.a., 4H, benzene); 7.37–7.59 (m, 2H, H$_5$,H6); 8.11 (d, 1H, H$_4$); 8.61 (d, 1H, H$_7$); 9.14 (s, 1H, H$_2$).
EM-DIP (70 eV) m/z (% Abundance): 398(M$^+$; 40); 223 (69); 161(100)

EXAMPLE 4

1-(benzo[b]thiophen-3-yl)-3-[4-(2-hydroxyphenyl) piperazin-1-yl]propan-1-one hydrochloride. (VN-221H)

M.p.: 292–294° C.
IR(cm$^{-1}$): 3235 (m, OH); 1659 (f, C=O); 1255 (m, Ar—O)
$^1$H-NMR (DMSO-d$_6$200 MHz) δ(ppm): 3.06 (t, 2H, CO—CH$_2$—CH$_2$); 3.26–3.76 (m, 8H, (CH$_2$)$_4$—N); 3.77 (t, 2H, CH$_2$—CO); 6.74–6.93 (m, 4H, benzene); 7.45–7.59 (m, 2H, H$_5$,H$_6$); 8.13 (dd, 1H, H$_7$); 8.61 (dd, 1H, H$_4$); 9.12 (s, 1H, H$_2$); 9.38 (s,1H, OH).
EM-DIP (70 eV) m/z (% Abundance): 398(M$^+$; 40); 223 (69); 161(100)

EXAMPLE 5

1-(3,5-dimethylbenzo[b]thiophen-2-yl)-3-[4-(2-methoxyphenyl)piperazin-1-yl]propan-1-one hydrochloride. (VN-7112)

M.p.: 86–87° C.
IR (KBr) (cm$^{-1}$): 1671 (f, C=O).
$^1$H-NMR (DMSO-d$_6$, 200 MHz) δ:2.42 (s, 3H, CH$_3$, C$_5$); 2.67 (s, 3H, CH$_3$,C$_3$); 2.97–3.21 (m, 8H, (CH$_2$)$_3$—N+ CH$_2$CO); 3.34–3.62 (m, 4H, (CH$_2$)$_2$—N—Ar); 6.81–7.02 (m, 4H, benzene); 7.36 (d, 1H, H$_6$); 7.75 (s, 1H, H$_4$); 7.85 (d, 1H, H$_7$).
EM-DIP (70 eV) m/z (% Abundance): 408(M$^+$, 1); 190(7); 189(42); 216(79).

EXAMPLE 6

1-(3-methylbenzo[b]thiophen-2-yl)-3-[4-(2-methoxyphenyl)piperazin-1-yl]propan-1-one hydrochloride. (VN-7012)

M.p.: 190–193° C.
IR (KBr) (cm$^{-1}$): 1723 (f, C=O).

$^1$H-NMR (DMSO-d$_6$, 200 MHz) δ:2.63 (s, 3H, CH$_3$,C$_3$); 2.77–3.11 (m,8H, (CH$_2$)$_3$—N+CH$_2$CO); 3.35–3.52 (s.a., 4H, (CH$_2$)$_2$—N—Ar); 3.79 (s, 3H, CH$_3$O);
6.78–7.10 (m, 4H, benzene); 7.50–7.58 (m, 2H, H$_6$+H$_5$); 8.05 (d, 2H, H$_4$+H$_7$)
EM-DIP (70 eV) m/z (% Abundance): 394(M$^+$, 1); 175(28); 150(100).

EXAMPLE 7

1-(3-methylbenzo[b]thiophen-2-yl)-3-[4-(2-hydroxyphenyl) piperazin-1-yl]propan-1-one hydrochloride. (VN-701H)

M.p.: 207–210° C.
IR (KBr) (cm$^{-1}$): 3406 (m, C—OH); 1775 (f, C═O).
$^1$H-NMR (DMSO-d$_6$, 200 MHz) δ:2.77 (s, 3H, CH$_3$,C$_3$); 3.06–3.77 (m, 12H, CH$_2$); 6.71–7.91 (m, 4H, benzene); 7.47–7.62 (m, 2H, H$_6$+H$_5$); 8.03 (d, 2H, H$_4$+H$_7$); 9.36 (s, 1H, OH)
EM-DIP (70 eV) m/z (% Abundance): 380(M$^+$, 5); 175(56); 147(63); 120(100).
Process B

EXAMPLE 8

3-[4-(2-methoxyphenyl)piperazin-1-yl]-1-(5-nitrobenzo[b]thiophen-3-yl)propan-1-one hydrochloride. (VN-8012)

1. 5-nitrobenzo[b]thiophen-2-carboxylic acid ethyl ester
   15 g (80.8×10$^{-3}$ moles) of 2-chloro-5-nitrobenzaldehyde dissolved in EtOH were added dropwise to a solution of 19.41 g (80.8×10$^{-3}$ moles) of Na$_2$S.9H$_2$O in EtOH at 40° C. It was held under reflux for 2 hours and thereafter 9 ml (80.8×10$^{-3}$ moles) of ethyl bromoacetate were added. After 2 hours at 50° C., Et$_3$N was added to pH=8–9. The mixture was left to react overnight at room temperature. The yellow product was collected by filtration. A further amount of product precipitated out on adding H$_2$O to the filtrate. It was purified by recrystallisation in hexane/AcOEt. Yield: 75%.
M.p.: 165° C.
IR (cm$^{-1}$): 1714 (mf, C═O); 1533–1505, 1334–1258 (mf, NO$_2$)
$^1$H-NMR (CDCl$_3$, 200 MHz) δ(ppm): 1.36 (t, 3H, CH$_3$—CH$_2$—O); 4.38 (c, 2H, CH$_3$—CH$_2$—O); 8.28 (s, 2H, H$_6$+H$_7$); 8.36 (s, 1H, H$_3$); 8.92 (s,1H, H$_4$)
EM-DIP (70 eV) m/z (% Abundance): 251(82); 206(100); 160(45)
2. 5-nitro-benzo[b]thiophen-2-carboxylic acid
   10 g (39.8×10$^{-3}$ moles) 5-nitrobenzo[b]thiophen-2-carboxylic acid ethyl ester in 250 ml of EtOH and 60 ml of H$_2$O were reacted with 3.8 g (67.8×10$^{-3}$ moles) of KOH at 60° C. for 2 hours, after which the potassium salt of the product was collected by filtration. A further fraction of the product was collected on adding isopropanol to the filtrate. The salt was dissolved in water and after acidulating the solution with HCl(c), the protonated form of the acid was precipitated out. It was purified by recrystallisation in H$_2$O/EtOH. Yield: 85%.
M.p.: 238° C.
IR (cm$^{-1}$): 1688 (mf, C═O); 1532, 1357–1307 (mf, NO$_2$)
$^1$H-NMR (DMSO-d$_6$; 200 MHz) δ(ppm): 8.30 (s, 2H, H$_6$+H$_7$); 8.32 (s, 1H, H$_3$); 8.96 (s, 1H, H$_4$)
EM-DIP (70 eV) m/z (% Abundance): 223 (100)
3. 5-nitrobenzo[b]thiochene
   5 g (22.4×10$^{-3}$ moles) of 5-nitro-benzo[b]thiophen-2-carboxylic acid in 105 ml of quinoline were heated, together with 5.2 g of powdered copper to a temperature of 180–190° C. for 45 minutes. The reaction mixture was filtered under vacuum and the filter was washed with ethyl ether. The mixture was extracted with ethyl ether twice, the phases being allowed to decant well, and the ethereal phase was washed with HCl 6N until no quinoline remains were left. It was dried with Na$_2$SO$_4$, the solvent was removed and the product was purified by recrystallisation in hexane/isopropanol. Yield: 65%.
M.p.: 150° C.
IR (cm$^{-1}$): 1714 (mf, C═O); 1533–1505, 1334–1258 (mf, NO$_2$)
$^1$H-NMR (CDCl$_3$, 200 MHz) δ(ppm): 7.43 (d, 1H, H$_3$); 7.59 (d, 1H, H$_2$); 7.91 (d, 1H, H$_7$); 8.13 (dd, 1H, H$_6$); 8.65 (d, 1H, H$_4$)
EM-DIP (70 eV) m/z (% Abundance): 179(100); 133(68).
4. 3-chloro-1-(5-nitro-benzo[b]thiophen-3-yl)-propan-1-one
   A solution of 1 g (5.58×10$^{-3}$ moles) of 5-nitrobenzo[b]thiophene and 0.65 ml (6.64×10$^{-3}$ moles) of 2-chloropropionyl chloride dissolved in 40 ml of dry chloroform was added dropwise over 650 mg of aluminum trichloride, dissolved in 20 ml dry chloroform under a nitrogen atmosphere. The mixture was left to react for 24 hours at room temperature and an additional amount of 650 mg of aluminum trichloride and 0.65 ml of 2-chloropropionyl chloride was added. After 48 hours reaction 100 ml of HCl 1.5N were added, followed by decantation and the organic phase was subsequently washed with a dilute solution of NaHCO$_3$, with H$_2$O and with a saturated solution of NaCl. It was dried with Na$_2$SO$_4$, the solvent was removed and it was purified in a silica column using hexane/toluene (25:75) as mobile phase. Yield: 30%.
M.p.: 128° C.
IR (cm$^{-1}$): 1670 (mf, C═O); 1510, 1335 (mf, NO$_2$)
$^1$H-NMR (CDCl$_3$, 200 MHz) δ(ppm): 3.51 (t, 2H, CH$_2$—C═O); 3.98 (t, 2H, CH$_2$—Cl); 7.99 (d, 1H, H$_7$); 8.29 (dd, 1H, H$_6$); 8.49 (s,1H, H$_2$); 9.64 (d, 1H, H, H$_4$)
EM-DIP (70 eV) m/z (% Abundance): 269(17); 206(100)
5. 3-[4-(2-methoxyphenyl)piperazin-1-yl]-1-(5-nitrobenzo[b]thiophen-3-yl)propan-1-one hydrochloride.
   To 600 mg of (5-nitrobenzo[b]thiophen-3-yl)-3-chloropropan-1-one (2.26×10$^{-3}$ moles) dissolved in 30 ml of THF were added 1.3 g of 2-methoxyphenylpiperazine (6.78×10$^{-3}$ moles) and 244 mg of Na$_2$CO$_3$ (2.26×10$^{-3}$ moles). After stirring for 72 hours at room temperature completion of the reaction was checked by TLC. The THF was removed and the residue was poured over water/ice, was extracted with AcOEt, the organic phase was washed with H$_2$O and a saturated solution NaCl and the solvent was removed. The residue was purified in a silica column using AcOEt/hexane (1:1) as mobile phase. Yield: 75%.
M.p.: 208–210° C.
IR (cm$^{-1}$): 1679 (mf, C═O); 1516–1333 (mf, NO$_2$); 1250 (mf, Ar—O—).
$^1$H-NMR (DMSO-d$_6$200 MHz) δ(ppm): 3.01–3.76 (m, 12H, —CH$_2$—); 3.80 (s, 3H, —O—CH$_3$); 6.86–7.03 (m, 4H, benzene); 8.30 (dd, 1H, H$_6$); 8.43 (d, 1H, H$_7$); 9.3 (s, 1H, H$_2$); 9.40 (d,1H, H$_4$).
EM-DIP (70 eV) m/z (% Abundance): 425(M$^+$; 10); 206 (68); 150(100).

Using the process described in Example 8, the following compounds were prepared from the corresponding chloropropanone:

EXAMPLE 9

1-(5-fluorobenzo[b]thiophen-3-yl)-3-[4-(2-methoxyphenyl)piperazin-1-yl]propan-1-one dihydrochloride. (VN-8512)

M.p.: 197° C.
IR (cm$^{-1}$): 1669 (mf, C═O); 1241 (mf, Ar—O—)

$^1$H-NMR (DMSO-d$_6$ 200 MHz) δ(ppm): 3.16 (s.a., 4H, (CH$_2$)$_2$—N—Ar); 3.38–3.57 (s.a., 6H, (CH$_2$)$_2$N+COCH$_2$); 3.73 (t, 2H, COCH$_2$CH$_2$); 3.78 (s, 3H, O—CH$_3$); 6.85–6.98 (m, 4H, benzene); 7.39 (ddd, 1H, H$_6$, J$_{46}$=2.5, J$_{47}$=8.3); 8.16 (dd, 1H, H$_7$, J$_{F7}$=5.2); 8.28 (d, 1H, H$_4$, J$_{F4}$=10.7); 9.20 (s, 1H, H$_2$).
EM-DIP (70 eV) m/z (% Abundance): 398 (M$^+$; 86); 205 (58); 179 (100)

EXAMPLE 10

1-(5-chlorobenzo[b]thiophen-3-yl)-3-[4-(2-methoxyphenyl)piperazin-1-yl]propan-1-one hydrochloride (VN-8412)

M.p.: 238–239° C.
IR (cm$^{-1}$): 1669 (mf, C=O); 1241 (mf, Ar—O—).
$^1$H-NMR (DMSO-d$_6$ 200 MHz) δ(ppm): 3.06–3.12 (m, 4H, —CH$_2$N$^4$); 3.54 (s.a., 6H, CH2N1+COCH$_2$); 3.75 (t, 2H, COCH$_2$CH$_2$); 3.80 (s, 3H, O—CH$_3$); 6.91–7.00 (m, 4H, benzene); 7.55 (dd, 1H, H$_6$ J$_{46}$=1.8, J$_{67}$=8.2); 8.19 (d, 1H, H$_7$); 8.61 (d, 1H, H$_4$); 9.19 (s, 1H, H$_2$).
EM-DIP (70 eV) m/z (% Abundance): 415 (M$^+$; 72); 205 (53); 195 (100).
Process C

EXAMPLE 11

1-(5-aminobenzo[b]thiophen-3-yl)-3-[4-(2-methoxyphenyl) piperazin-1-yl]propan-1-one dihydrochloride (VN-8112)

200 mg of 1-(5-nitrobenzo[b]thiophen-3-yl) piperazin-1-yl]propan-1-one dihydrochloride, obtained according to the process described in Example 8, were dissolved in 20 ml of THF with 100 mg of Ni-Raney and were subjected to a pressure of 50 p.s.i. H$_2$ and to a temperature of 40° C. for 2 hours, after which a further 100 mg of Ni-Raney were added. After 24 hours during which the reaction was kept under regular stirring, the disappearance of the starting product was observed in TLC using dichloromethane/MeOH (9:1). It was filtered over celite, the solvent was quickly removed to avoid possible oxidation and the residue was dissolved in 10 ml of ethyl ether and 2 ml of EtOH. The hydrochloride of the product precipitates on adding 0.1 ml of HCl(c). The solid was washed with hot acetone and the product was filtered. Yield: 57%.
M.p.: 200–201° C.
IR (cm$^{-1}$): 3354 (m, NH$_2$); 1667 (mf, C=O); 1245 (mf, Ar—O—).
$^1$H-NMR (DMSO-d$_6$ 200 MHz) δ(ppm): 3.04–3.75 (m, 12H, —CH$_2$—); 3.79 (s, 3H, —O—CH$_3$); 6.89–7.06 (m, 4H, benzene); 7.48 (dd, 1H, H$_6$); 8.21 (d, 1H, H$_7$); 8.60 (d, 1H, H$_4$); 9.23 (s,1H, H$_2$).
EM-DIP (70 eV) m/z (% Abundance): 395 (M$^+$; 2.2); 176 (40); 150 (100).

PROCESS OF SYNTHESIS OF FORMULA (1b) PRODUCTS

EXAMPLE 12

1-(benzo[b]thiophen-3-yl)-3-[4-(2-methoxyphenyl) piperazin-1-yl]propan-1-ol (VN-2222)

To 500 mg of 1-(benzo[b]thiophen-3-yl)-3-[4-(2-methoxyphenyl)piperazin-1-yl]propan-1-one hydrochloride (1.20×10$^{-3}$ moles) in 30 ml of MeOH a 0° C. was added NaBH$_4$ for about 20 min until the reaction ceased to evolve. After two hours 50 ml of H$_2$O were added to the medium, it was stirred for a few minutes and was extracted twice with 200 ml of AcOEt. The organic phase was washed three times with H$_2$O, was dried with Na$_2$SO$_4$ and the solvent was removed. It was purified in silica column with AcOEt/hexane (1:1). The free base was thus obtained in form of a white solid. Yield: 30%. Two polymorphic forms of this product were obtained, the melting points of which were 108° C. and 120° C. respectively.
IR (cm$^{-1}$): 3220 (m, OH); 1243 (mf, Ar—O—)
$^1$H-NMR (CDCl$_3$ 200 MHz) δ(ppm): 2.06–2.13 (m, 2H, CH$_2$—CHOH); 2.68–2.88 (m, 6H, (CH$_2$)$_3$—N); 3.16 (s.a., 4H, (CH$_2$)$_2$—N—Ar); 3.87 (s, 3H, OCH$_3$); 6.89–7.00 (m, 4H, benzene) 7.21–7.39 (m, 2H, H$_5$+H$_6$); 7.42 (s, 1H, H$_2$); 7.77–7.86 (m, 2H, H$_4$+H$_7$)
EM-DIP (70 eV) m/z (% Abundance): 368(M$^+$; 6.8); 120 (100)

Using the process described in the Example 12 and stalting out from the corresponding ketones described in Examples 1 to 11 the following products were prepared, either in the form of a free base or as a hydrochloride by subsequent precipitation in HCl (c):

EXAMPLE 13

3-[4-(2-methoxyphenyl)piperazin-1-yl]-1-(5-nitrobenzo[b]thiophen-3-yl)propan-1-ol monohydrate dihydrochloride (VN-8022)

M.p.: 130–131° C.
IR (cm$^{-1}$): 3404 (m, OH); 1510–1330 (mf, NO$_2$); 1245 (mf, Ar—O—).
$^1$H-NMR (DMSO-d$_6$ 200 MHz) δ(ppm): 2.09 (m, 2H, CHOH—CH$_2$); 3.06–3.29 (m, 6H, (CH$_2$)$_3$—N); 3.46–3.61 (m, 4H, (CH$_2$)$_2$N—Ar); 3.79 (s, 3H, OCH$_3$); 5.17 (dd, 1H, CHOH); 6.93–6.99 (m, 4H, benzene); 7.96 (s, 1H, H$_2$); 8.20 (dd, 1H, H$_6$); 8.31 (d,1H, H$_7$); 8.90 (d,1H, H$_4$).
EM-DIP (70 eV) m/z (% Abundance): 427 (M$^+$; 61); 219 (100).

EXAMPLE 14

1-(5-methylbenzo[b]thiophen-3-yl)-3-[4-(2-methoxyphenyl)piperazin-1-yl]propan-1-ol dihydrochloride. (VN-8322)

M.p.: 109–111° C.
IR (cm$^{-1}$): 3425 (m, OH); 1245 (mf, Ar—O—).
$^1$H-NMR (CDCl$_3$ 200 MHz) δ(ppm): 2.08 (dd, 2H, CO—CH$_2$); 2.43 (s, 3H, CH$_3$); 2.65–2.88 (m, 6H, (CH$_2$)$_3$—N); 3.14 (s.a. 4H, (CH$_2$)$_2$—N—Ar); 3.85 (s, 3H, O—CH$_3$); 5.29 (t,1H, CHOH); 6.70 (s.a. 1H, OH); 6.83–7.08 (m, 4H, benzene); 7.15 (dd, 1H, H$_6$); 8.21 (d,1H, H$_7$); 8.60 (d,1H, H$_4$); 9.23 (s,1H, H$_2$).
EM-DIP (70 eV) m/z (% Abundance): 396(M$^+$; 27); 205 (100).

EXAMPLE 15

1-(benzo[b]thiophen-3-yl)-3-[4-(4-fluoro-2-methoxyphenyl)piperazin-1-yl]propan-1-ol hydrochloride. (VN-222F)

M.p.: 109–111° C.
IR (cm$^{-1}$): 3425 (m, OH); 1245 (mf, Ar—O—)
$^1$H-NMR (CDCl$_3$ 200 MHz) δ(ppm): 2.08 (dd, 1H, CO—CH$_2$); 2.43 (s, 3H, CH$_3$); 2.65–2.88 (m, 6H, (CH$_2$)$_3$—N); 3.14 (s.a. 4H, (CH$_2$)$_2$—N—Ar); 3.85 (s, 3H, O—CH$_3$); 5.29 (t, 1H, CHOH); 6.70 (s.a. 1H, OH); 6.83–7.08 (m, 4H, benzene); 7.15 (dd, 1H, H$_6$); 8.21 (d,1H, H$_7$); 8.60 (d,1H, H$_4$); 9.23 (s, 1H, H$_2$)
EM-DIP (70 eV) m/z (% Abundance): 396(M$^+$; 27); 205 (100)

EXAMPLE 16

1-(benzo[b]thiophen-3-yl)-3-[4-(2-hydroxphenyl)piperazin-1-yl]propan-1-ol (VN-222H)

M.p.: 109–111° C.
IR (cm$^{-1}$): 3220 (m, OH); 1243 (mf, Ar—O—)
$^1$H-NMR (CDCl$_3$ 200 MHz) δ(ppm): 2.04–2.16 (m, 2H, CHOH—CH$_2$); 2.65–2.83 (m, 6H, (CH$_2$)$_3$—N); 2.97 (t, 4H,(CH$_2$)$_2$—N—Ar); 5.36 (dd, 1H, CHOH); 6.70 (s.a. 1H, OH); 6.83–7.19 (m, 4H, benzene); 7.30–7.41 (m, 2H, H$_5$+H$_6$); 7.44 (s, 1H, H$_2$); 7.78–7.89 (m, 2H, H$_4$+H$_7$)
EM-DIP (70 eV) m/z (% Abundance): 368(M$^+$; 6.8); 120 (100)

EXAMPLE 17

1-(benzo[b]thiophen-3-yl)-3-[4-(4-chlorophenyl)piperazin-1-yl]propan-1-ol. (VN-2225)

M.p.: 148–150° C.
IR (cm$^{-1}$): 3150 (m, OH); 1230 (mf, Ar—O—)
$^1$H-NMR (CDCl$_3$ 200 MHz) δ(ppm): 1.99 (t, 2H, CHOH—CH$_2$); 2.52–2.70 (m, 6H, (CH$_2$)$_3$—N); 3.10 (t, 4H, (CH$_2$)$_2$—N—Ar); 5.23 (t, 1H, CHOH); 6.72 (d, 2H$_2$,+H$_6$'); 7.11 (d, 2H, H$_3$+H$_4$); 7.25 (d, 2H, H$_5$+H$_6$); 7.32 (s, 1H, H$_2$); 7.67–7.78 (m, 2H, H$_4$+H$_7$)
EM-DIP (70 eV) m/z (% Abundance): 386(M$^+$, 38); 209 (100).

EXAMPLE 18

1-(3,5-dimethylbenzo[b]thiophen-2-yl)-3-[4-(2-methoxyphenyl)piperazin-1-yl]propan-1-ol (VN-7122)

M.p.: 79–80° C.
IR (KBr) (cm$^{-1}$): 3415 (f, OH); 1499 (m, C—N); 1240 (m, C—O).
$^1$H-NMR (DMSO-d$_6$, 200 MHz) δ: 1.77–1.97 (m, 2H, CHOH—CH$_2$); 2.29 (s, 3H, CH$_3$(C$_5$); 2.42 (s, 3H, CH$_3$(C$_3$); 2.44–2.52 (s.a., 6H, (CH$_2$)$_3$—N); 2.88–3.12 (s.a., 4H, (CH$_2$)$_2$—N—Ar; 3.75 (s, 3H, CH$_3$O); 5.12–5.20 (s.a., 1H, CHOH); 5.80–5.92 (s.a.,1H, OH); 6.85 (d, 4H, benzene); 7.15 (d, 1H, H$_6$); 7.45 (s, 1H, H$_4$); 7.7 (d, 1H, H$_7$)
EM-DIP (70 eV) m/z (% Abundance): 410(M$^+$, 76); 200 (100); 148(16).

EXAMPLE 19

1-(3-methylbenzo[b]thiophen-2-yl)-3-[4-(2-methoxyphenyl)piperazin-1-yl]propan-1-ol. (VN-7022)

M.p.: 145–147° C.
IR (KBr) (cm$^{-1}$): 3405 (m,OH); 1498 (m,C—N).
$^1$H-NMR (DMSO-d$_6$, 200 MHz) δ: 1.82–1.95 (m, 2H, CHOH—CH$_2$); 2.33 (s, 3H, CH$_3$—Ar); 2.38–2.52 (s.a., 6H, (CH$_2$)$_3$—N); 2.90–3.05 (s.a., 4H, (CH$_2$)$_2$—N—Ar); 3.75 (s, 3H, CH$_3$O); 5.12–5.20 (s.a., 1H, CHOH); 5.91 (s, 1H, OH); 6.90 (d, 4H, benzene); 7.26–7.40 (m, 2H, H$_6$+H$_5$); 7.69(d, 1H, H$_4$); 7.88 (d, 1H, H$_7$)
EM-DIP (70 eV) m/z (% Abundance): 396(M$^+$, 68); 219 (41); 205(100);134 (31).

EXAMPLE 20

1-(3-methylbenzo[b]thiophen-2-yl)-3-[4-(2-hydroxyphenyl)piperazin-1-yl]propan-1-ol. (VN-702H)

M.p.: 149–151° C.
IR (KBr) (cm$^{-1}$): 3398 (m, OH); 1490 (f, C—N).
$^1$H-NMR (DMSO-d$_6$, 200 MHz): 1.79–1.96 (m, 2H, CHOH—CH$_2$); 2.34 (s, 3H, CH$_3$); 2.43–2.57 (s.a, 6H, (CH$_2$)$_3$—N); 2.90–3.12 (s.a., 4H, (CH$_2$)$_2$—N—Ar); 5.19 (t, 1H, CHOH); 6.66–6.87 (m, 5H, benzene+OH); 7.27–7.41 (m, 2H, H$_6$+H$_5$); 7.70 (d, 1H, H$_4$); 7.90 (d,1H, H$_7$).
EM-DIP (70 eV) m/z (% Abundance): 382(M$^+$, 77); 134 (100); 120(79).

EXAMPLE 21

1-(5-chlorobenzo[b]thiophen-3-yl)-3-[4-(2-methoxyphenyl)piperazin-1-yl]propan-1-ol dihydrochloride. (VN-8422)

M.p.: 185–190° C.
IR (cm$^{-1}$): 1241 (mf, Ar—O—)
$^1$H-NMR (CDCl$_3$ 200 MHz) δ(ppm): 1.93 (t, 2H, CHOHCH$_2$); 2.65–2.88 (m, 6H, (CH$_2$),N); 3.14 (s.a., 4H, (CH$_2$)$_2$—N—Ar); 3.85 (s, 3H, O—CH$_3$); 5.29 (t, 1H, CHOH); 5.83 (s.a., 1H, OH); 6.74–6.96 (m, 4H, benzene); 7.18 (dd, 1H, H$_6$, J$_{46}$=1.5, J$_{67}$=8.7); 7.36 (d, 1H, H$_2$); 7.63 (d, 1H, H$_7$) ; 7.70 (d, 1H, H$_4$)
EM-DIP (70 eV) m/z (% Abundance): 417 (M$^+$; 4); 205 (100)

EXAMPLE 22

1-(5-fluorobenzo[b]thiophen-3-yl)-3-[4-(2-methoxyphenyl)piperazin-1-yl]propan-1-ol dihydrochloride. (VN-8522)

M.p.: 125° C.
IR (cm$^{-1}$): 3401 (d, OH); 1241 (mf, Ar—O—)
$^1$H-NMR (CDCl$_3$ 200 MHz) δ(ppm): 2.02–2.11 (t, 2H, CHOHCH$_2$); 2.68–2.87 (m, 6H, (CH$_2$)$_3$N); 3.15 (s.a., 4H, (CH$_2$)$_2$—N—Ar); 3.86 (s, 3H, O—CH$_3$); 5.26 (t, 1H, CHOH); 6.84–7.01 (m, 4H, benzene); 7.08 (dd, 1H, H$_6$, J$_{46}$=2.2, J67=8.8); 7.49 (s, 1H, H$_2$); 7.50 (d, 1H, H$_7$, J$_{F4}$=10.0); 7.75 (d,1H, H$_4$, J$_{F7}$=4.8)
EM-DIP (70 eV) m/z (% Abundance): 3857 (3); 205 (100)

PROCESSES OF SYNTHESIS OF FORMULA (1c) PRODUCTS

EXAMPLE 23

1-(benzo[b]thiophen-3-yl)-3-[4-(2-methoxyphenyl)piperazin-1-yl]propan-1-one E-oxime. (VN-2282)

0.5 g of 1-(benzo[b]thiophen-3-yl)-3-[4-(2-methoxyphenyl)piperazin-1-yl]propan-1-one hydrochloride (1.20×10$^{-3}$ moles) in 20 ml of EtOH and 0.5 g of hydroxylamine hydrochloride (7.19×10$^{-3}$ moles) were refluxed for 1.5 hours. After this time, the reaction was basified with NaOH dissolved in EtOH and H$_2$O and was allowed to react for 1 hour under reflux. H$_2$O was added to the medium, the excess EtOH was removed in the rotary evaporator and the aqueous phase was extracted with AcOEt. The organic phase was washed with H$_2$O, dried with Na$_2$SO$_4$ and the solvent was removed. The product was purified with a silica column using AcOEtthexane as mobile phase. In this way the E isomer of the oxime was prepared. Yield: 60%.
M.p.: 191° C.
IR (cm$^{-1}$): 3426 (f, OH); 1242 (mf, Ar—O)
$^1$H-NMR (CDCl$_3$ 200 MHz) δ(ppm): 2.60 (s.a., 6H, (CH$_2$)$_3$—N ); 2.95–3.16 (m, 6H, (CH$_2$)$_2$N, CH$_2$NOH); 3.77 (s; 3H, OCH$_3$) 6.87–6.92 (m, 4H, benzene); 7.40–7.43 (m, 2H, H$_5$+H$_6$); 8.01 (dd, 1H,H$_7$); 8.10 (s, 1H, H$_2$); 8.57 (dd, 1H, H$_4$); 11.31 (s, 1H, OH)
EM-DIP (70 eV) m/z (% Abundance): 395(M$^+$; 4,1); 379 (5,4); 205 (100)

The following products are prepared by a process similar to the one described in Example 23.

EXAMPLE 24

1-(3,5-dimethylbenzo[b]thiophen-2-yl)-3-[4-(2-methoxyphenyl)piperazin-1-yl]propan-1-one oxime. (VN-7182)

M.p.: 72–74° C.
IR (KBr) (cm$^{-1}$): 3421 (f, N—OH); 1450 (m,C—N).
$^1$H-NMR (DMSO-d$_6$, 200 MHz) δ: 2.42–2.63 (s.a., 14H, (CH$_2$)$_3$—N+2CH$_3$[3+5]+CH$_2$CH$_2$NOH); 2.80–2.98 (s.a., 4H, CH$_2$)$_2$N); 3.73 (s, 3H, CH$_3$O—); 6.88 (d, 4H, benzene); 7.19 (d, 1H, H$_6$); 7.57 (s, 1H, H$_4$); 7.71–7.80 (m, 1H, H$_7$); 11.4–11.8 (s.a., 1H, OH).
EM-DIP (70 eV) m/z (% Abundance): 425(M$^+$, 2); 407(6); 205(100).

EXAMPLE 25

1 (3-methylbenzo[b]thiophen-2-yl)-3-[4-(2-methoxyphenyl) piperazin-1-yl]propan-1-one oxime. (VN-7082)

M.p.: 82–84° C.
IR (KBr) (cm$^{-1}$): 3652 (p,N—OH); 1498 (f,C—N).
$^1$H-NMR (DMSO-d$_6$, 200 MHz) δ: 2.48–2.62 (s.a., 14H, (CH$_2$)$_3$—N—CH$_3$+CH$_2$NOH ); 2.85–3.03 (s.a., 4H, (CH$_2$)$_2$N); 3.77 (s, 3H, CH$_3$O); 6.85–7.02 (d, 4H, benzene); 7.35–7.50 (m, 2H, H$_5$+H$_6$); 7.79–7.85 (m, 1H, H$_4$); 7.90–7.99 (m, 1H, H$_7$); 11.52–11.82 (s.a., 1H, OH)
EM-DIP (70 eV) m/z (% Abundance): 409(M$^+$, 13); 393 (25); 205(100).

EXAMPLE 26

Enantiomeric resolution of the product 1-(benzo[b]thiophen-3-yl)-3-[4-(2-methoxyphenyl)piperazin-1-yl]-propan-1-ol (VN-2222)

Chloroform (2 ml), triethylamine (538 µl, 3.88 mmoles) and 4-dimethylaminopyridine (108 mg, 0.88 mmoles) were added to each of two test tubes containing 500 mg (1.31 mmoles) of the racemic mixture of VN-2222. These solutions were added over two flasks containing respectively 531 mg (2.88 mmoles) and 542 mg (2.94 mmoles) of (S)-(+)-α-methoxyphenylacetic acid chloride. They were allowed to react for one hour and were pooled into one flask, with the addition of chloroform up to 50 ml. The mixture was washed with: dilute HCl (50 ml×3), dilute Na$_2$CO$_3$ (50 ml×3), saturated NaCl (50 ml×2), H$_2$O (50 ml×2). The chloroform was removed at reduced pressure, giving an oil corresponding to the mixture of diastereomers (R)-VN-2222-(S)-OMM and (S)-VN-2222(S)-OMM (880 mg, 1.66 mmoles).
HPLC [HPLC Waters 600E; LED detector Waters 994; work station Millennium; Supelcosil LC-CN column, 25×0.46 cm; mobile phase: (hexane/isopropanol+triethylamine, 90/10); flow rate: 0.7 ml/min]: dwell time (t$_r$) in minutes; 8.2 diastereomer (R)-VN-2222-(S)-OMM and 9.3 diastereomer (S)-VN-2222-(S)-OMM.

Thereafter, the mixture of diastereomers dissolved in ethyl acetate was separated by preparative TLC using 20×40 cm silica gel 60 plates. Mobile phase: TDA (Toluene, dioxane, acetic acid 90:25:4). Two bands appear at 8 cm (S, S) and 12 cm (R,S) (UV: 254 nm). Ethyl acetate was added to the silica corresponding to each diastereomer, followed by filtration and the solvent was removed at reduced pressure. Both diastereomers were obtained separately: 420 mg (0.79 mmoles) of (R,S) and 375 mg (0.71 mmoles) of (S,S).

(R)-VN-2222-(S)-OMM:
$^1$H-NMR(CDCl$_3$, 200 MHz) δ(ppm): 2.06–2.23 (m, 4H, CHOH—CH$_2$+CH$_2$—N); 2.44 (m, 4H, (CH$_2$)$_2$—N); 3.02 (m, 4H, (CH$_2$)$_2$N—Ar); 3.37 (s, 3H, CH$_3$O-OMM); 3.83 (s, 3H, CH$_3$O); 4.77 (s, 1H, OMM); 6.36 (t, 1H, CHOH—OMM); 6.81–6.99 (m, 4H, benzene); 7.33–7.51 (m, 8H, H$_2$+H$_5$+H$_6$+5H benzene OMM); 7.69–7.89 (m, 2H, H$_4$+H$_7$).
HPLC: t$_r$: 8.2 min.
(S)-VN-2222-(S)-OMM:
$^1$H-NMR(CDCl$_3$, 200 MHz) δ(ppm): 2.23–2.26 (m, 2H, CHOH—CH$_2$); 2.38–2.43 (m, 2H, CH$_2$—N); 2.59 (m, 4H, (CH$_2$)$_2$—N); 3.07 (m, 4H, (CH$_2$)$_2$N—Ar); 3.38 (s, 3H, CH$_3$O—OMM); 3.84 (s, 3H, CH$_3$O); 4.83 (s, 1H, OMM); 6.34 (t, 1H, CHOH—OMM); 6.83–6.99 (m, 5H, benzene+H$_2$); 7.24–7.40 (m, 7H, H$_5$+H$_6$+5H benzene OMM); 7.69–7.80 (m, 2H, H$_4$+H$_7$).
HPLC: t$_r$: 9.3 min The next step was hydrolysis under non-racemising conditions. Each of the diastereomers was dissolved in methanol (40 ml), an excess of K$_2$CO3 was added, and the reaction mass was held at room temperature under constant stirring for 5 hours. The K$_2$CO$_3$ was removed by filtration, the solvent was removed, water was added and extractions in chloroform (3×50 ml) were carried out. The chloroform was removed at reduced pressure, yielding 172 mg (0.45 mmoles) of the enantiomer (R) and 97 mg (0.25 mmnoles) of the enantiomer (S). Both enantiomers have the same $^1$H-NMR spectrum.
VN-2222: $^1$H-NMR(CDCl$_3$, 200 MHz) δ(ppm): 2.09 (C, 2H, CHOH—CH$_2$); 2.6–2.9 (m, 6H, (CH$_2$)$_3$N); 3.1–3.3 (m, 4H, (CH$_2$)$_2$N—Ar); 3.86 (s, 3H, OCH$_3$); 5.35 (t, 1H, CHOH); 7.01–7.31 (m, 4H, benzene); 7.4 (m, 2H, H$_5$+H$_6$); 7.44 (d, 1H, H$_2$); 7.78–7.789 (m, 2H, H$_4$+H$_7$)
HPLC: t$_r$: 12 min.

To determine enantiomeric purity, each enantiomer was derived with (R)-(+)-α-methoxy-a-(trifluoromethyl)phenylacetic acid chloride. Two vials were prepared with 5 mg (0.013 mmoles) of each enantiomer, chloroform (2 ml), triethylamine (6 µl, 0.039 mmoles) and 4-dimethylaminopyridine (2 mg, 0.016 mmoles). Two solutions were obtained, which were added over each of the flasks containing the (R)-(+)-α-methoxy-α-(trifluoromethyl)phenylacetic acid chloride (2 ml of hexane, N, N-dimethylformamide (4 µl, 0,05 mmoles) and oxalyl chloride (19 µl, 0,20 mmoles) were added to two vials containing (R)-(+)-α-methoxy-α-(trifluoromethyl)phenylacetic acid (10 mg, 0,043 mmoles), were left to react for one hour, were filtered and the solvent was removed, yielding the chloride of the acid, 7,1 mg (0.03 mmoles) and 7.0 mg (0.03 mmoles), respectively). Both flasks were allowed to rest for one hour, followed by the addition of 10 ml of chloroform. They were washed with: dilute HCl (10 ml×3), dilute Na$_2$CO$_3$ (10 ml×3), saturated NaCl (10 ml×2), H$_2$O (10 ml×2). The chloroform was removed, yielding in each case an oil corresponding to each of the diastereomers: (1R)-1-(benzo[b]thiophen-3-yl)-3-[4-(2-methoxyphenyl)piperazin-1-yl]propyl-(2R)-3,3,3-trifluoro-2-methoxy-2-phenylacetate, 4.2 mg (0.007 mmoles), and (1S)-1-(benzo[b]thiophen-3-yl)-3-[4-(2-methoxyphenyl)piperazin-1-yl]propyl-(2R)-3,3,3-trifluoro-2-methoxy-2-phenylacetate, 4 mg (0.007 mmoles).
(R)-VN-2222-(R)-MTPA:
$^1$H-NMR(CDCl$_3$, 200 MHz) δ(ppm): 2.10–2.48 (m, 4H, CHOH—CH$_2$+CH$_2$—N); 2.52 (m, 4H, (CH$_2$)$_2$—N); 3.01 (m, 4H, (CH$_2$)$_2$—N—Ar); 3.47 (c, 3H, CH$_3$O-MTPA); 3.84(s, 3H, CH$_3$O); 6.49 (t, 1H, CHOH—MTPA); 6.77–7.01 (m, 4H, benzene); 7.15–7.37 (m, 8H, H$_2$+H$_5$+H$_6$+5H benzene MTPA); 7.73–7.82 (m, 2H, H$_4$+H$_7$).

HPLC: $t_r$: 6.3 min.
(S)-VN-2222-(R)-MTPA:
$^1$H-NMR(CDCl$_3$, 200 MHz) δ(ppm): 2.10–2.48 (m, 4H, CHOH–CH$_2$+CH$_2$—N); 2.52 (m, 4H, (CH$_2$)$_2$—N); 3.01 (m, 4H, (CH$_2$)$_2$—N—Ar); 3.35 (c, 3H, CH$_3$O—MPTA); 3.84 (s, 3H, CH$_3$O); 6.44 (t, 1H, CHOH—MTPA); 6.77–7.01 (m, 4H, benzene); 7.15–7.37 (m, 8H, H$_2$+H$_5$+H$_6$+5H benzene MTPA); 7.73–7.82 (m, 2H, H$_4$+H7).
HPLC: $t_r$: 6.3 min.

DESCRIPTION OF THE METHODS USED TO EVALUATE THE PHARMACOLOGICAL PROPERTIES

Test for Binding to 5HT$_{1A}$ Receptors

To determine the affinity of the products to the 5HT$_{1A}$ receptors. binding tests were carried out, using as radioligand the agonist $^3$H-dipropylaminotetraline (DPAT) following the technique described by Hoyer et al. (Eur. J. Pharmacol., 118, 13–23) (1985).

Rat front cortex was dried and homogenised in Tris-HCl 50 mM pH 7.7 at 4° C. The resulting homogenate was centrifuged at 25.000 r.p.m. for 15 min. and the pellet obtained was resuspended in Tris-HCl and incubated at 37° C. for 10 min. The resulting resuspension was centrifuged again and resuspended in Tris-HCl containing CaCl$_2$ 4 mM. For the binding test, the incubation mixture contained the membrane suspension, $^3$H-DPAT (1 nM) and the cold displacer. Rapid filtration was carried out to separate the fraction bound to the receptors.

Binding Tests to the 5-HT Carrier

The rat front cortex membrane fraction was prepared as described for the determination of the binding to the 5-HT$_{1A}$ receptors. The membrane suspension was incubated for 60 min at 22° C. with $^3$H-paroxetine using fluoxetine as displacer. On completion of the incubation, the membrane fraction was separated by rapid filtration. The technique used is the one described by Marcusson et al. (J. Neurochemistry, 44, 705–711) (1985).

The results obtained in these pharmacological evaluation tests for the products of the present invention are summarised in Tables 1 and 2.

TABLE 1

Derivatives of benzothiophen substituted in the 3-position

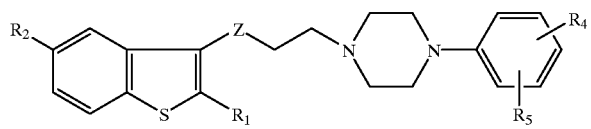

| PRODUCT | Z | R$_1$ | R$_2$ | R$_4$ | R$_5$ | 5HT$_{1A}$ IC$_{50}$ (M) | Carrier 5-HT IC$_{50}$ (M) |
|---|---|---|---|---|---|---|---|
| VN-2212 Example 3 | \C=O/ | H | H | 2-OCH$_2$ | H | $8.9 \times 10^{-8}$ | $2.1 \times 10^{-7}$ |
| VN-221H Example 4 | \C=O/ | H | H | 2-OH | H | $2.2 \times 10^{-7}$ | $9.8 \times 10^{-7}$ |
| VN-8012 Example 8 | \C=O/ | H | NO$_2$ | 2-OCH$_3$ | H | $3.5 \times 10^{-7}$ | $4.6 \times 10^{-7}$ |
| VN-2222 Example 12 | \CHOH/ | H | H | 2-OCH$_3$ | H | $4 \times 10^{-8}$ | $4.10^{-8}$ |
| VN-2225 Example 17 | \CHOH/ | H | H | 4-Cl | H | $10^{-5}$ | $1.10^{-7}$ |
| VN-2282 Example 23 | \C=N—OH/ | H | H | 2-OCH$_3$ | H | $1.2 \times 10^{-7}$ | $1.9 \times 10^{-7}$ |

TABLE 1-continued

Derivatives of benzothiophen substituted in the 3-position

| PRODUCT | Z | $R_1$ | $R_2$ | $R_4$ | $R_5$ | IC$_{50}$ (M) 5HT$_{1A}$ | Carrier 5-HT |
|---|---|---|---|---|---|---|---|
| VN-221F Example 2 | \C=O/ | H | H | 2-OCH$_3$ | 4F | | |
| VN-222F Example 15 | \CHOH/ | H | H | 2-OCH$_3$ | 4F | | |
| VN-222H Example 16 | \CHOH/ | H | H | 2-OH | H | $3.6 \times 10^{-8}$ | $8.10^{-8}$ |
| VN-8022 Example 13 | \CHOH/ | H | NO$_2$ | 2-OCH$_3$ | H | | |
| VN-8112 Example 11 | \C=O/ | H | NH$_2$ | 2-OCH$_3$ | H | $5.6 \times 10^{-8}$ | $1.2 \times 10^{-6}$ |
| VN-8312 Example 1 | \C=O/ | H | CH$_3$ | 2-OCH$_3$ | H | $1.4 \times 10^{-7}$ | $6.5 \times 10^{-7}$ |
| VN-8322 Example 14 | \CHOH/ | H | CH$_3$ | 2-OCH$_3$ | H | | |
| VN-8422 Example 21 | \CHOH/ | H | Cl | 2-OCH$_3$ | H | $6 \times 10^{-8}$ | $6 \times 10^{-8}$ |
| VN-8512 Example 9 | \C=O/ | H | F | 2-OCH$_3$ | H | $3.1 \times 10^{-8}$ | $2 \times 10^{-7}$ |
| VN-8522 Example 22 | \CHOH/ | H | F | 2-OCH$_3$ | H | $2.35 \times 10^{-9}$ | $2.4 \times 10^{-8}$ |

TABLE 2

Derivatives of benzothiophenes substituted in the 2-position.

[Structure: benzothiophene with R2 at 5-position, R1 at 3-position, 2-position linked via Z-CH2CH2-piperazine-phenyl(R4,R5)]

| PRODUCT | Z | $R_1$ | $R_2$ | $R_4$ | $R_5$ | $IC_{50}$ (M) $5HT_{1A}$ | Carrier 5-HT |
|---|---|---|---|---|---|---|---|
| VN-7012 Example 6 | \C=O/ | $CH_3$ | H | 2-$OCH_3$ | H | $4 \times 10^{-7}$ | $2 \times 10^{-6}$ |
| VN-7112 Example 5 | \C=O/ | $CH_3$ | $CH_3$ | 2-$OCH_3$ | H | $2.1 \times 10^{-7}$ | $3 \times 10^{-7}$ |
| VN-7022 Example 19 | \CHOH/ | $CH_3$ | H | 2-$OCH_3$ | H | $4.4 \times 10^{-7}$ | $8 \times 10^{-7}$ |
| VN-701H Example 7 | \C=O/ | $CH_3$ | H | 2-OH | H | $5.6 \times 10^{-7}$ | $10^{-5}$ |
| VN-7122 Example 18 | \CHOH/ | $CH_3$ | $CH_3$ | 2-$OCH_3$ | H | $1.7 \times 10^{-7}$ | $2.4 \times 10^{-7}$ |
| VN-702H Example 20 | \CHOH/ | $CH_3$ | H | 2-OH | H | $4 \times 10^{-7}$ | $1.1 \times 10^{-7}$ |
| VN-7082 Example 25 | \C=N—OH/ | $CH_3$ | H | 2-$OCH_3$ | H | $7.6 \times 10^{-7}$ | $2 \times 10^{-6}$ |
| VN-7182 Example 24 | \C=N—OH/ | $CH_3$ | $CH_3$ | 2-$OCH_3$ | H | $8.7 \times 10^{-7}$ | $5.5 \times 10^{-6}$ |

What is claimed is:

1. A benzothiophene compound of formula (1):

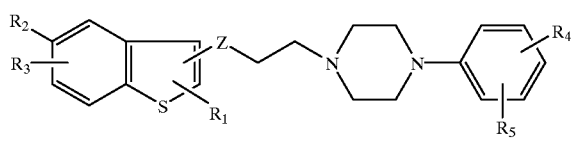

(I)

where:

Z is: —CO—, —CH($OR_6$)—, —C($NOR_7$)—;

$R_1$ is: H, low molecular weight alkyl, halogen, or —$OR_6$;

$R_2$ and $R_3$ are independent and stand for: H, $C_1$–$C_6$ alkyl, halogen, —$OR_8$, nitro, cyano, $NR_9R_{10}$; —$COR_8$; $CO_2R_8$; —$SO_2NR_9R_{10}$; —$SO_2R_8$; $SR_8$; —$CONR_9R_{10}$;

$R_4$ and $R_5$ are the same or different and each stands for: H, low molecular weight alkyl, halogen, haloalkyl, —$OR_8$, nitro, $NR_8R_{10}$; —$COR_8$; $CO_2R_8$; —$SO_2NR_8R_{10}$; —$SO_2R_8$; $SR_8$, cyano; —$CONR_9R_{10}$ or $R_4$ and $R_5$ may form together a benzene ring fused to the phenyl ring;

—$R_6$ is: H, $C_1$–$C_6$ alkyl, $CO_2R_8$, —C(O)$NR_9R_{10}$, naphthyl or phenyl optionally substituted by one or more substituents selected from among the following: H, haloalkyl, alkyl, halogen, low molecular weight alkoxy, methylenedioxy, nitro, cyano;

$R_7$ is: H or $C_1$–$C_6$ alkyl; —$R_8$ is: H, low molecular weight alkyl or phenyl; —$R_9$ and $R_{10}$ are independent and stand for:

H, low molecular weight alkyl or phenyl, or a salt, a hydrate, a geometric isomer, an optical isomer, or a polymorph thereof.

2. The compound of claim 1, wherein formula (1) is:
1-(benzo[b]thiophen-3-yl)-3-[4-(2-methoxyphenyl) piperazin-1-yl]propan-1-one
1-(3,5-dimethylbenzo[b]thiophen-2-yl)-3-[4-(2-methoxyphenyl)piperazin-1-yl]propan-1-one
1-(5-fluorobenzo[b]thiophen-3-yl)-3-[4-(2-methoxyphenyl) piperazin-1-yl]propan-1-one
—1-(5-chlorobenzo[b]thiophen-3-yl)-3-[4-(2-methoxyphenyl)piperazin-1-yl]propan-1-one.

3. The compound of claim 1, where formula (1) is:
1-(benzo[b]thiophen-3-yl)-3-[4-(2-methoxyphenyl) piperazin-1-yl]propan-1-ol
1-(benzo[b]thiophen-3-yl)-3-[4-(2-hydroxyphenyl) piperazin-1-yl]propan-1-ol
1-(3,5-dimethylbenzo[b]thiophen-2-yl)-3-[4-(2-methoxyphenyl)piperazin-1-yl]propan-1-ol or
1-(3-methylbenzo[b]thiophen-2-yl)-3-[4-(2-hydroxyphenyl) piperazin-1-yl]propan-1-ol
1-(5-clorobenzo[b]thiophen-3-yl)-3-[4-(2-methoxyphenyl) piperazin-1-yl]propan-1-ol
1-(5-fluorobenzo[b]thiophen-3-yl)-3-[4-(2-methoxyphenyl) piperazin-1-yl]propan-1-ol.

4. The compounds of claim 1, where formula (1) is
1-(benzo[b]thiophen-3-yl)-3-[4-(2-methoxyphenyl) piperazin-1-yl]propan-1-one oxime.

5. A pharmaceutical composition comprising a compound according to any one of claims 1 to 4, in a therapeutic amount for the treatment of neurological disorders.

6. A pharmaceutical composition comprising a compound according to one of claims 1 to 4, in a therapeutically active amount for the treatment of anxiety and/or depression and an adequate amount of a carrier.

7. A method for treating anxiety or depression, comprising administering a therapeutically effective amount of a compound according to one of claims 1 to 4 to a patient in need thereof.

\* \* \* \* \*